United States Patent [19]
Som

[11] Patent Number: 6,077,865
[45] Date of Patent: Jun. 20, 2000

[54] TOPICAL ANTIFUNGAL FORMULATION CONTAINING TOLNAFTATE

[76] Inventor: Kamales Som, 6351 Athena Dr., Huntington Beach, Calif. 92647

[21] Appl. No.: 09/263,159

[22] Filed: Mar. 5, 1999

[51] Int. Cl.[7] .................................................... A31K 31/27
[52] U.S. Cl. ............................................................. 514/481
[58] Field of Search .................................... 514/390, 383, 514/384, 481

[56] References Cited

U.S. PATENT DOCUMENTS

| | | | |
|---|---|---|---|
| 4,348,407 | 9/1982 | Imondi et al. ........................... | 514/480 |
| 4,810,498 | 3/1989 | DiMeglio .............................. | 424/195.1 |
| 5,322,695 | 6/1994 | Shah et al. .............................. | 424/448 |
| 5,519,059 | 5/1996 | Sawaya .................................... | 514/599 |
| 5,661,170 | 8/1997 | Chodosh .................................. | 514/390 |

*Primary Examiner*—William R. A. Jarvis
*Assistant Examiner*—Vickie Kim
*Attorney, Agent, or Firm*—Gene Scott-Patent Law & Venture Group

[57] ABSTRACT

An antifungal preparation for topical use is described containing tolnaftate and a quaternary ammonium compound. The formulation contains tolnaftate at a pharmaceutical effective concentration along with a quaternary ammonium compound such as benzalkonium chloride along with other ingredients. The resultant product is dramatically faster acting and significantly more potent than known tolnaftate formulations alone.

2 Claims, No Drawings

//  6,077,865

TOPICAL ANTIFUNGAL FORMULATION CONTAINING TOLNAFTATE

BACKGROUND OF THE INVENTION

1. Field of the Invention

This invention relates generally to topical pharmaceutical formulations, and more particularly to a topical formulation combination of ingredients for use in combating fungal infections, the formulation including tolnaftate as an active agent and benzalkonium chloride as a preservative.

2. Description of Related Art

The following art defines the present state of this field:

Levin, U.S. Pat. No. 5,656,301 describes a topical composition comprising LYCD together with known topically active useful medicinal agents such as anti-wrinkling, antibiotic, anticancer, antifungal, anti-inflammatory such as anti-acne, antiviral, wound healing, and hair-growing agents. The LYCD works together with the other active agents to achieve a synergistic result more effective than can be obtained from the topical agents individually, and more effective than could be predicted from the mere addition of the known efficacies of the individual ingredients.

Levin, U.S. Pat. No. 5,656,300 describes a topical composition comprising LYCD together with known topically active useful medicinal agents such as anti-wrinkling, antibiotic, anticancer, antifungal, anti-inflammatory such as anti-acne, antiviral, wound healing, and hair-growing agents. The LYCD works together with the other active agents to achieve a synergistic result more effective than can be obtained from the topical agents individually, and more effective than could be predicted from the mere addition of the known efficacies of the individual ingredients.

Levin, U.S. Pat. No. 5,023,090 describes a topical composition comprising LYCD together with known topically active useful medicinal agents such as anti-wrinkling, antibiotic, anticancer, antifungal, anti-inflammatory such as anti-acne, antiviral, wound healing, and hair-growing agents. The LYCD works together with the other active agents to achieve a synergistic result more effective than can be obtained from the topical agents individually, and more effective than could be predicted from the mere addition of the known efficacies of the individual ingredients.

Levin, U.S. Pat. No. 5,714,169 describes a topical composition comprising LYCD together with known topically active useful medicinal agents such as anti-wrinkling, antibiotic, anticancer, antifungal, anti-inflammatory such as anti-acne, antiviral. Wound healing, and hair-growing agents. The LYCD works together with the other active agents to achieve a synergistic result more effective than can be obtained from the topical agents individually, and more effective than could be predicted from the mere addition of the known efficacies of the individual ingredients.

Levin, U.S. Pat. No. 5,667,810 describes a topical composition comprising LYCD together with known topically active useful medicinal agents such as anti-wrinkling, antibiotic, anticancer, antifungal, anti-inflammatory such as anti-acne, antiviral, wound healing, and hair-growing agents. The LYCD works together with the other active agents to achieve a synergistic result more effective than can be obtained from the topical agents individually, and more effective than could be predicted from the mere addition of the known efficacies of the individual ingredients.

Levin, U.S. Pat. No. 5,676,973 describes a topical composition comprising LYCD together with known topically active useful medicinal agents such as anti-wrinkling, antibiotic, anticancer, antifungal, anti-inflammatory such as anti-acne, antiviral would healing, and hair-growing agents. The LYCD works together with the other active agents to achieve a synergistic result more effective than can be obtained from the topical agents individually, and more effective than could be predicted from the mere addition of the known efficacies of the individual ingredients.

Benzalkonium chloride, a mixture of alkylbenzyldimethylammonium chlorides in which the alkyls are long chain compounds ($C_8$ to $C_{18}$), and related quaternary ammonium chlorides, have been used as surface-active germicides for many pathogenic non-sporulating bacteria and fungi and as antimicrobial agents in cosmetics and pharmaceutical products as described in U.S. Pat. No. 5,492,932. They have also been used in formulations in combination with protease inhibitors, as skin treatment agents, as taught in U.S. Pat. No. 5,346,886.

Formulations containing tolnaftate (o-2-Naphthyl m,N-dimethylthiocarbanilate) have been used extensively to treat various topical fungal infections. There are several related pharmaceutical preparations for topical use including lotions and sprays containing tolnaftate as an active agent. These products are available commercially as Aftate® aerosol liquid, Desenex® spray liquid, Tinactin® liquid and lotion and other products; see U.S. Pat. No. 5,519,059. Products containing tolnaftate in combination with cortisone have been developed for topical use against fungal infection as described in U.S. Pat. No. 5,496,812. Finally, preparations containing tolnaftate have also been developed to treat the infection of herpes simplex virus as shown in U.S. Pat. No. 4,438,134.

The prior art teaches topical formulations for the treatment of fungal and other infections. However, the prior art does not teach that the combination of tolnaftate and benzalkonium chloride may be used to significant advantage as a preferred agent for combating fungal infection. The present invention teaches this highly effective, yet unknown combination and provides further related advantages as described in the following summary.

SUMMARY OF THE INVENTION

The present invention teaches certain benefits in formulation and use which give rise to the objectives described below.

The present invention provides a pharmaceutical topical formulation comprising tolnaftate and benzalkonium chloride, or other quaternary ammonium compound with other ingredients to form a fungal infection agent with highly improved properties. The present invention is a formulated topical antifungal lotion containing tolnaftate as the active ingredient with a quaternary ammonium compound, specifically benzalkonium chloride as a preservative and catalyst. The formulation is faster acting and more potent than products containing only tolnaftate. Tolnaftate is widely used as an antifungal agent and benzalkonium chloride is widely used as an antimicrobial agent or preservative. However, a combination of these ingredients has not been known to have superior properties in antifungal preparations. The combination of these two agents has been discovered to be faster acting and also more potent than each ingredient alone. In fact, the improvements have been shown to be so dramatic as to be clearly an important improvement in this area of pharmacology and medicine.

A primary objective of the present invention is to provide a topical antifungal agent having advantages not taught by the prior art.

Another objective is to provide such an agent that is significantly faster acting than comparable topical agents in the prior art.

A still further objective is to provide such an agent that is significantly more potent than prior art products containing only tolnaftate as an active ingredient.

Other features and advantages of the present invention will become apparent from the following more detailed description, taken in conjunction with the accompanying drawings, which illustrate, by way of example, the principles of the invention.

DETAILED DESCRIPTION OF THE INVENTION

As stated, tolnaftate is a well known topical antifungal agent and benzalkonium chloride is well known as a microbial agent and in other uses. The present invention is a topical preparation for the effective treatment of fungal infections such as athlete's foot (tinea pedis) and jock itch (tinea cruris). The active ingredient is tolnaftate, preferably at a concentration of between approximately 0.05 and 1.5 percent for nonprescription use, in combination with benzalkonium chloride as an antimicrobial preservative and catalyst. The formulation also contains emollients and moisturizers for the benefit of the treated skin areas. Other quaternary compounds can be used as a replacement for benzalkonium chloride with similar effects. The preferred embodiment of the present invention contains the following constituents in concentration level ranges as shown to the right:

| CONSTITUENT | PERCENT BY WEIGHT |
|---|---|
| tolnaftate | 0.5–4.0 |
| cetaryl alcohol | 0.2–6.0 |
| emulsifying wax | 0.1–5.0 |
| propylene glycol | 0.5–7.0 |
| cetyl trimethyl ammonium chloride | 0.5–5.0 |
| cetyl alcohol | 0.2–3.0 |
| cetaryl octnoate | 0.2–2.0 |
| stearyl alcohol | 0.2–3.0 |
| olyl alcohol | 0.3–3.0 |
| octoxynol - 9 | 0.1–2.0 |
| benzalkonium chloride | 0.05–3.0 |
| imidazolidinyl urea | 0.1–1.0 |
| methylparaben | 0.1–0.5 |
| water | 70–90 |

Specifically, the present invention is an antifungal active formulation comprising, an antifungal agent comprising tolnaftate and an antimicrobial agent comprising a quaternary ammonium compound. Preferably, the formulation of the antifungal agent and the antimicrobial agent are combined in an aqueous topical ointment. Further, the formulation comprises at least one skin emollient and at least one skin moisturizer as described above. Preferably, the quaternary ammonium compound is benzalkonium chloride. Preferably, the tolnaftate comprises between approximately 0.5 and 4.0 percent, by weight of the formulation, and the benzalkonium chloride comprises between approximately 0.05 and 3.0 percent by weight of the formulation. Generally, the antimicrobial agent is taken from the class of quaternary ammonium compounds including benzethonium chloride, benzalkonium chloride, octyl-decyl-dimethyl ammonium chloride, didecyl-dimethyl ammonium chloride, cetyl-pyridinium chloride, tetradecyl-pyridinium bromide and other quaternary ammonium bromides. The basis of the claims of this application is that the Federal Drug Administration, and Medicine in general does not recognize quaternary ammonium compounds as beneficial for fungal infection. Therefore, compounds such as benzalkonium chloride have been used only to avoid microbial infection as in a topical wash for open wounds in first aide. On the other hand it is well known that antifungal ingredients such as tolnaftate are too slow to be effective in fighting microbial infection. Thus, it is not known to combine these two types of ingredients. It would not be expected that the combination of an antifungal agent and an antimicrobial agent could be effective against fungal infection, however, surprising results occur when the two active ingredients are combined and this has been shown in clinical studies as described by Dr. Rory Jaye Friedman, D.P.M. in a declaration submitted herewith. The inventive combination has been shown to be effective on a greater range of patients and to give results significantly faster as well.

The method of preparation of the formulation of the present invention is critical to its functional properties and is therefore an important feature of the present invention. If prepared in a manner significantly different from the following, experimental results show a marked lessening in potency and speed of action.

Initially, a first mixture is formed by combining the constituents: tolnaftate, cetaryl alcohol, emulsifying wax, cetyl alcohol, stearyl alcohol, olyl alcohol and methyl paraben in a first vessel and these constituents are heated until the mixture forms a clear liquid. Next, a second mixture is formed by mixing the remaining constituents into the water which has been pre-heated to a temperature of between 75 and 85 degrees Centigrade, the constituents comprising: cetyl trimethyl ammonium chloride, octoxynol-9, imidazolidinyl urea, and the quaternary ammonium compound. The second mixture is thoroughly mixed for approximately ten minutes. Finally, the first mixture is added to the second mixture and stirred gently for approximately 15 minutes. The result is a smooth lotion of homogeneous composition when cooled to room temperature.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A method of preparation of a topical antifungal formulation comprising the sequential steps of:
    a) combining quantities of tolnaftate, cetaryl alcohol, emulsifying wax, cetyl alcohol, stearyl alcohol, olyl alcohol and methyl paraben in a first vessel to form a first mixture;
    b) heating the first mixture until the first mixture forms a clear liquid;
    c) heating a quantity of water to between 75 and 85 degrees Centigrade in a second vessel;
    d) combining quantities of cetyl trimethyl ammonium chloride, octoxynol-9, imidazolidinyl urea, and the quaternary ammonium compound into the heated water of the second vessel to form a second mixture;
    e) mixing the second mixture for approximately 10 minutes;
    f) combining the first and the second mixtures in the second vessel thoroughly;
    g) stirring the combined mixture in the second vessel for approximately 15 minutes and cooling to room temperature to achieve a smooth lotion of homogeneous composition.

2. A topical antifungal formulation comprising tolnaftate 0.5–4.0 percent by weight, cetaryl alcohol 0.2–6.0 percent by weight, emulsifying wax 0.1–5.0 percent by weight, propylene glycol 0.5–7.0 percent by weight, cetyl trimethyl ammonium chloride 0.5–5.0 percent by weight, cetyl alcohol 0.2–3.0 percent by weight, cetaryl octnoate 0.2–2.0 percent by weight, stearyl alcohol 0.2–3.0 percent by weight, olyl alcohol 0.3–3.0 percent by weight, octoxynol 0.1–2.0 percent by weight, benzalkonium chloride 0.05–3.0 percent by weight, imidazolidinyl urea 0.1–1.0 percent by weight, methyl paraben 0.1–0.5 percent by weight, and the balance being water.

* * * * *